United States Patent [19]

Gontarz et al.

[11] 3,994,869

[45] Nov. 30, 1976

[54] PHOTODEGRADABLE POLYOLEFINS CONTAINING ARYL-SUBSTITUTED 1,3-DIONES

[75] Inventors: John A. Gontarz, Landenberg; Charles H. Nelson, West Chester, both of Pa.

[73] Assignee: ICI United States Inc., Wilmington, Del.

[22] Filed: Feb. 18, 1975

[21] Appl. No.: 550,446

[52] U.S. Cl. ............................ 526/1; 260/DIG. 43; 526/54; 526/55; 526/352; 526/914; 526/22
[51] Int. Cl.$^2$............................................. C08J 3/20
[58] Field of Search............... 260/DIG. 43, 32.8 A, 260/94.9 GC, 93.7

[56] References Cited
UNITED STATES PATENTS

| | | | |
|---|---|---|---|
| 3,797,690 | 3/1974 | Taylor et al. | 260/DIG. 43 |
| 3,846,395 | 11/1974 | Harper et al. | 260/DIG. 43 |
| 3,852,227 | 12/1974 | Matsuda et al. | 260/DIG. 43 |
| 3,888,804 | 6/1975 | Swanholm et al. | 260/DIG. 43 |

*Primary Examiner*—Eugene C. Rzucidlo

[57] ABSTRACT

Aryl substituted 1,3-diones have been found to be useful as accelerators for the photodegradation of polyolefins.

4 Claims, No Drawings

PHOTODEGRADABLE POLYOLEFINS CONTAINING ARYL-SUBSTITUTED 1,3-DIONES

BACKGROUND OF THE INVENTION

1. Field of the Invention

The present invention relates generally to polyolefin compositions which are capable of being degraded upon exposure to light. More particularly, the present invention relates to polyolefin compositions which are degraded upon exposure to visible or ultraviolet light, said compositions comprising in addition to a polyolefin an aryl substituted 1,3-dione.

2. Description of the Prior Art

Polyolefins and copolymers thereof have previously been used as packaging materials and in agricultural applications, the latter including, for example, mulching films and seed tapes. It is known that these polymers undergo degradation and become fragile when exposed, for prolonged periods of time, to sunlight or other forms of ultraviolet radiation and, for many applications, radiation absorbing agents are added to the polymers in order to stabilize said materials and retard such aging. However, for many other applications, particularly those mentioned above, it is desirable to accelerate the aging of the film. This is particularly true in applications such as mulching films used in agriculture and horticulture and in disposable packaging applications such as films, bags, bottles, hollow articles, and cellulose sheet materials such as paper, cardboard, or regenerated cellulose which are coated or lined with polyolefins.

A variety of additives have previously been suggested for incorporation in polyolefin materials to accelerate the degradation thereof. However, to be useful on a practical, commercial scale the additive must result in a polyolefin composition having sufficient stability for its intended use as well as the capability of degrading in a reasonable period of time after use.

SUMMARY OF THE INVENTION

In accordance with the present invention, photodegradable polyolefin compositions are prepared comprising a polyolefin and aryl substituted 1,3-dione represented by the following formula:

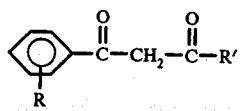

wherein
R is selected from the group consisting of hydrogen, halogen, $C_1$ to $C_9$ alkyl, and $C_1$ to $C_9$ alkoxy; and
R' is selected from the group consisting of $C_1$ to $C_{17}$ alkyl, cycloalkyl containing from 4 to 7 carbon atoms, and substituents represented by the following formula

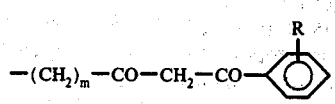

wherein
m is an integer equal to from 1 to about 8 and
R is defined above.

DESCRIPTION OF THE PREFERRED EMBODIMENTS

As mentioned above, the present invention relates to compositions comprising a polyolefin and an aryl substituted 1,3-dione. Each of these components is described in detail below.

Polyolefins

Any polyolefin known in the art may be utilized in the improved compositions of the present invention. As is well known, the term polyolefin refers to a class of polymers derived from polymerization of relatively simple olefins -- i.e., unsaturated alphatic hydrocarbons represented by the general formula $C_nH_{2n}$ wherein n is an integer. The polyolefins which may be employed in the photodegradable compositions of the present invention include, for example, polyethylene, polypropylene, polybutylene and other homopolymers as well as copolymers of these olefins either with each other or with other alpha-olefins such as 1-octene and 1-octadecene. Particularly useful copolymers include those prepared from ethylene and propylene, butene or isoprene. If polyethylene is employed, it may be either of the high density or low density type.

Diones

As was mentioned above, the photodegradable compositions of the present invention include, in addition to a polyolefin, an aryl substituted 1,3-dione. The diones which have been found to be useful in accordance with the present invention are those which may be represented by the formula:

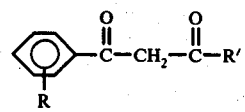

wherein
R is selected from the group consisting of hydrogen, halogen, $C_1$ to $C_9$ alkyl, and $C_1$ to $C_9$ alkoxy; and
R' is selected from the group consisting of $C_1$ to $C_{17}$ alkyl, cycloalkyl containing from 4 to 7 carbon atoms, and substituents represented by the following formula:

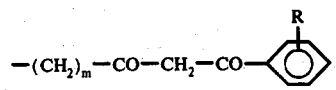

wherein
m is an integer equal to from 1 to about 8 and
R is as defined above.

These diones are known in the art and may be prepared, for example, by reacting acetophenone or a substituted acetophenone with an ester in the presence of a suitable base in accordance with the following reaction wherein R and R' are as defined above and A is an alkyl group, preferably methyl or ethyl.

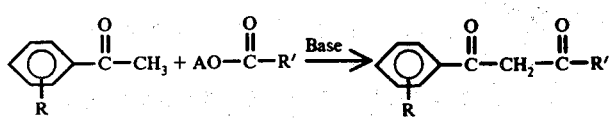

As mentioned above, in addition to acetophenone, substituted materials such as those represented by the following formula

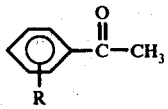

wherein R is as defined above, may be employed. Substituted acetophenones which may be utilized include, for example, orthobromoacetophenone, para-bromoacetophenone, orthochloroacetophenone, para-chloroacetophenone, paramethylacetophenone, paramethoxyacetophenone, paranonylacetophenone, paranonoxyacetophenone.

Representative esters which may be utilized in the preparation of these compounds include for example, methyl stearate, ethyl benzoate, ethyl acetate and ethyl laurate. The base employed in accordance with the present invention, includes, for example, sodium methoxide, sodium ethoxide and sodium hydride. However, any base which is both soluble in the particular solvent employed and capable of abstracting a proton from the acetophenone may be utilized. The reaction is carried out by combining the above-mentioned ingredients in a suitable aprotic solvent such as toluene or tetrahydrofuran. The resulting reaction mixture is stirred and the product recovered therefrom by methods which are known in the art.

Alternatively, the diones are conveniently prepared by reacting an alkyl ketone with an aromatic ester in accordance with the following reaction wherein R, R' and A are as defined above.

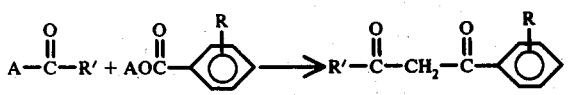

As will be apparent to those skilled in the art, the enol form of the above diones may also be employed in the compositions of the present invention. In the enol form, the additives may be represented by one of the following formulas wherein R and R' are as defined above.

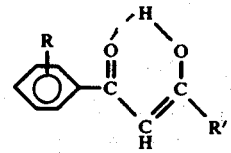

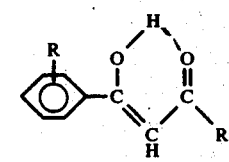

In the preparation of the photodegradable compositions of the present invention, the dione is combined with a polyolefin by any suitable means. The aryl substituted 1,3-dione may be incorporated into the polymer by any of the techniques known for blending a solid or a liquid with a polymer prior to formation of the polymer into the form in which it will be used. For example, the desired amounts of the additive can be dry-blended with the polymer or the additive as a solution or dispersion can be mixed with a solution or dispersion of the polymer in a suitable solvent. The amount of dione employed in the preparation of said photodegradable compositions should be equal to from about 0.05 percent to about 1.0 percent by weight based on the total weight of said composition.

It has been found that preferred results are achieved if the polyolefin and dione are combined in a suitable solvent. The solvent employed should have a low boiling point so that it may be conveniently removed from the resulting composition and it also must dissolve the dione. After the polyolefin and dione are combined in the solvent, the solvent is removed, resulting in a composition comprising the polyolefin and dione. Representative solvents which may be employed in the preparation of said composition include, for example, methylene chloride and chloroform.

The resulting composition may be used in the preparation of films and molded articles as well as in coatings which are applied to a variety of substrates. Preferably, the composition is formed into film of any desired thickness by conventional methods including, for example, by extrusion of the molten material into a tube or cast film, by casting a solution of the polymer in a suitable solvent onto a rotating drum or by other methods. The thickness of the film may vary over a wide range depending upon the use for which the film is intended. As mentioned above, the advantage of the compositions of the present invention is that, when exposed to either visible or ultraviolet light, the materials degrade. This degradation is indicated by the embrittlement of the composition upon exposure to radiation as defined above.

The compositions of the present invention are particularly useful in the preparation of mulching films for use in agricultural applications and in the preparation of seed tapes. They are also useful in disposable packages such as packaging films, bags and bottles.

In order to describe the present invention so that it may be more clearly understood, the folowing examples are set forth. These examples are set forth primarily for the purpose of illustration and any enumeration of detail contained therein should not be interpreted as a limitation on the concept of the present invention. In the examples all parts refer to parts by weight.

In the examples, the compositions were tested for degradability by preparing molded plaques therefrom on a conventional Carver press equipped with means for heating the plates thereof.

The radiation source employed in the examples was a conventional fluorescent sunlamp-blacklamp unit.

Embrittlement of the samples, i.e., degradation of the polymer, was determined by periodically removing a sample of the plaque prepared from the composition from the radiation source, bending said sample to 180°, and measuring the exposure time required until the sample when bent as indicated would break.

Examples 1 and 2 are representative of the preparation of diones which may be used in accordance with the present invention. The reamining examples illustrate compositions of the present invention and photodegradable materials prepared therefrom.

EXAMPLE 1

Into a suitable reaction vessel, there were added
59.8 grams (0.2 mol) of methyl stearate,
12.0 grams (0.22 mol) of sodium methoxide,
24.0 grams (0.2 mol) of acetophenone, and
50 ml of toluene.

The resulting solution was stirred at room temperature overnight. To the resulting slurry, there was added 100 ml of a 20 percent solution of hydrochloric acid; and the resulting mixture ws extracted with methylene chloride. The methylene chloride extract was washed with water, dried over magnesium sulfate, and concentrated to give an ivory colored solid. The solid was then recrystallized from methanol and dried resulting in 25 grams of product identified as 1-phenyleicosane-1,3-dione having a melting point of 64°–66° C.

Analysis of the product indicated 80.78 percent carbon and 10.94 percent hydrogen. These results compared favorably with the theoretical percentages calculated for $C_{26}H_{42}O_2$ as 80.77 percent carbon and 10.95 percent hydrogen.

EXAMPLE 2

Into a 500 ml four-necked round bottom flask, equipped with a mechanical stirrer, dropping funnel and thermometer, which had been purged with dry nitrogen and cooled in an ice bath to 2° C., there was added 18.5 grams of a 52 percent mineral oil dispersion of sodium hydride followed by 100 ml of dry tetrahydrofuran. There was then added 41 ml of ethylbenzoate over a period of 15 min. followed by 38 ml of pinacolone. All of the reagents had been dried over molecular sieves prior to use. The resulting reaction mixture was stirred for 4 hrs. at 0° C. and then allowed to warm to room temperature and stirred at room temperature overnight.

200 ml of 15 percent hydrochloric acid solution was added to the reaction mixture and the mixture was vigorously stirred for 1 hour. The organic phase was separated, washed with water and brine and filtered to yield a light orange solution. The resulting organic phase was distilled at atmospheric pressure to remove unreacted pinacolone and benzoic acid. The dark brown oil remaining in the still pot was analyzed by infrared and found to be primarily the desired product, namely, 1-phenyl-4,4-dimethylpentane-1,3-dione. This product was purified in accordance with the following procedure.

The material was distilled at atmospheric pressure and the main fraction boiling at from 273°–278° C. was collected and then redistilled under vacuum and a fraction having a boiling point of 145° C. at 8 mm of pressure was collected. After a second distillation the fraction removed at a boiling point of 116° C. at 3 mm of pressure was separated. 8.0 grams of this product were diluted in 25 ml of ethanol and then added, with stirring, to a solution of 9.5 grams of cupric acetate monohydrate in 20 ml of water. The resulting reaction mixture was heated to 80° C. and maintained at that temperature for 15 min. At the end of this time the reaction mixture was cooled to room temperature and the resulting green crystals were removed by filtration. The green crystals were recrystallized from petroleum ether, and dried resulting in 8 grams of a solid product having a melting point of 199°–201° C. The dried product was stirred with 50 ml of a 30 percent aqueous solution of magnesium sulfate at 50° C. for 1 hour. The aqueous solution was removed and the organic phase washed with water and passed through a column containing magnesium sulfate and activated carbon. The resulting clear solution was analyzed and found to contain 76.43 percent carbon and 7.85 percent hydrogen. This compared favorably with the calculated figures of 76.44 percent carbon and 7.90 percent hydrogen for the desired product.

EXAMPLE 3

A photodegradable composition was prepared by combining
100 parts of polypropylene,
0.5 parts calcium stearate, .05 parts of the product prepared in Example 1, and 100 parts of methylene chloride.

The composition was stirred and heated to remove the solvent. The sample of the resulting composition was then compression molded on a Carver press at 205° C. to form a sheet having a thickness of 0.06 inches. The resulting film was exposed to a fluorescent sunlamp-blacklamp unit and the time to embrittlement determined. This time was equal to 144 hours. By comparison, a control sample which did not contain the dione required 276 hours to become embrittled.

EXAMPLE 4

Employing the procedure described in Example 3, additional compositions were prepared by combining varying amounts of the dione prepared in Example 1 with polypropylene, preparing films therefrom, and testing as defined above. The results of these experiments are given in the following table:

TABLE I

| Example | Amount of Dione | Time to Embrittlement |
|---|---|---|
| 3 | 0.1% | 192 hours |
| 4 | 0.5% | 192 hours |
| 5 | 1.0% | 204 hours |

EXAMPLE 5

A photodegradable composition was prepared by combining,
100 parts of high density polyethylene,
0.5 parts calcium stearate,
100 parts of methylene chloride, and
varying amounts of the product prepared in Example 1 as indicated in the following table.

The composition was treated and sheets molded therefrom as described in Example 3. The resulting film was exposed to a fluorescent sunlamp-blacklamp unit and the time to embrittlement determined. The results on each of the sheets and on a control sample which did not contain the dione are also given in the following table.

TABLE II

| Parts of Dione | Embrittlement (Hours) |
|---|---|
| None | 1,476 |
| 0.05 | 1,004 |
| 0.10 | 788 |
| 0.15 | 576 |
| 1.0 | 478 |

EXAMPLE 6

Several additional diones useful in the present invention were also evaluated. The diones are identified in the following table.

TABLE III

| COMPOUND | NAME | STRUCTURE |
|---|---|---|
| 1 | 1-Phenylbutane-1,3-dione | Ph-C(O)-CH$_2$-C(O)-CH$_3$ |
| 2 | 1-(p-Methoxyphenyl)-butane-1,3-dione | MeO-C$_6$H$_4$-C(O)-CH$_2$-C(O)-CH$_3$ |
| 3 | 1-(p-Methoxyphenyl)-eicosane-1,3-dione | MeO-C$_6$H$_4$-C(O)-CH$_2$-C(O)-C$_{17}$H$_{35}$ |
| 4 | 1-Phenyltetradecane-1,3-dione | Ph-C(O)-CH$_2$-C(O)-C$_{11}$H$_{23}$ |
| 5 | 1-Phenyleicosane-1,3-dione | Ph-C(O)-CH$_2$-C(O)-C$_{17}$H$_{35}$ |
| 6 | 1-(p-Chlorophenyl)-butane-1,3-dione | Cl-C$_6$H$_4$-C(O)-CH$_2$-C(O)-CH$_3$ |
| 7 | 1-(p-Chlorophenyl)-eicosane-1,3-dione | Cl-C$_6$H$_4$-C(O)-CH$_2$-C(O)-C$_{17}$H$_{35}$ |
| 8 | 1-(p-Methylphenyl)-butane-1,3-dione | Me-C$_6$H$_4$-C(O)-CH$_2$-C(O)-CH$_3$ |
| 9 | 1-(p-Methylphenyl)-eicosane-1,3-dione | Me-C$_6$H$_4$-C(O)-CH$_2$-C(O)-C$_{17}$H$_{35}$ |
| 10 | 1-(m-Methylphenyl)-butane-1,3-dione | m-Me-C$_6$H$_4$-C(O)-CH$_2$-C(O)-CH$_3$ |

TABLE III-continued

| COMPOUND | NAME | STRUCTURE |
|---|---|---|
| 11 | 1-(m-Methylphenyl)-eicosane-1,3-dione | Me-C₆H₄-C(O)-CH₂-C(O)-C₁₇H₃₅ |
| 12 | 1-(p-t-Butylphenyl)-eicosane-1,3-dione | (t-Bu)-C₆H₄-C(O)-CH₂-C(O)-C₁₇H₃₅ |
| 13 | 1-(p-t-Butylphenyl)-butane-1,3-dione | (t-Bu)-C₆H₄-C(O)-CH₂-C(O)-CH₃ |
| 14 | 1-(p-Heptyloxyphenyl)-butane-1,3-dione | C₇H₁₅O-C₆H₄-C(O)-CH₂-C(O)-CH₃ |
| 15 | 1-(p-Heptyloxyphenyl)-eicosane-1,3-dione | H₁₅C₇O-C₆H₄-C(O)-CH₂-C(O)-C₁₇H₃₅ |
| 16 | 1-Phenyl-4,4-dimethyl pentane 1,3-dione | C₆H₅-C(O)-CH₂-C(O)-C(CH₃)₃ |

To a composition comprising
 100 parts of high density polyethylene,
 0.5 parts of calcium stearate, and
 100 parts of methylene chloride,
each of the above compounds was added at two amounts -- 0.5 parts and 1.0-parts. The compositions were stirred, heated and sheets were molded therefrom and tested as described in Example 3. The results are given in the following table.

TABLE IV

| Compound | Amount | Embrittlement (Hours) |
|---|---|---|
| None | — | 1,340 |
| 1 | 0.5 | 608 |
| 1 | 1.0 | 530 |
| 2 | 0.5 | 610 |
| 2 | 1.0 | 740 |
| 3 | 0.5 | 530 |
| 3 | 1.0 | 776 |
| 4 | 0.5 | 499 |
| 4 | 1.0 | 692 |
| 5 | 0.5 | 554 |
| 5 | 1.0 | 510 |
| 6 | 0.5 | 500 |
| 6 | 1.0 | 564 |
| 7 | 0.5 | 477 |
| 7 | 1.0 | 477 |
| 8 | 0.5 | 542 |
| 8 | 1.0 | 520 |
| 9 | 0.5 | 540 |
| 9 | 1.0 | 418 |
| 10 | 0.5 | 540 |
| 10 | 1.0 | 574 |
| 11 | 0.5 | 520 |
| 11 | 1.0 | 499 |
| 12 | 0.5 | 608 |
| 12 | 1.0 | 530 |
| 13 | 0.5 | 499 |
| 13 | 1.0 | 564 |
| 14 | 0.5 | 692 |
| 14 | 1.0 | 872 |
| 15 | 0.5 | 728 |
| 15 | 1.0 | 499 |
| 16 | 0.5 | 574 |
| 16 | 1.0 | 800 |

EXAMPLE 7

The diones identified in Example 6 were also evaluated in a composition comprising
 100 parts of polypropylene,
 0.5 parts of calcium stearate, and
 100 parts of methylene chloride.
Each of the compounds was added to this composition at 0.5 parts and at 1.0 parts and sheets were prepared as decribed in Example 3. The resulting films were placed outdoors and exposed to sunlight while oriented at a 45° angle to the south over a period of several days and the time to embrittlement determined. The results are given in the following table.

TABLE V

| Compound | Amount | Embrittlement (Hours) |
|---|---|---|
| — | — | 1,825 |
| 1 | 0.5 | 669 |
| 1 | 1.0 | 658 |
| 2 | 0.5 | 778 |
| 2 | 1.0 | 860 |
| 3 | 0.5 | 872 |
| 3 | 1.0 | 1,690 |
| 4 | 0.5 | 689 |
| 4 | 1.0 | 800 |
| 5 | 0.5 | 709 |
| 5 | 1.0 | 718 |
| 6 | 0.5 | 658 |
| 6 | 1.0 | 525 |
| 7 | 0.5 | 689 |
| 7 | 1.0 | 678 |
| 8 | 0.5 | 668 |
| 8 | 1.0 | 586 |
| 9 | 0.5 | 678 |
| 9 | 1.0 | 699 |
| 10 | 0.5 | 778 |
| 10 | 1.0 | 836 |
| 11 | 0.5 | 585 |
| 11 | 1.0 | 679 |
| 12 | 0.5 | 669 |
| 12 | 1.0 | 679 |
| 13 | 0.5 | 718 |
| 13 | 1.0 | 936 |
| 14 | 0.5 | 1,124 |
| 14 | 1.0 | 1,402 |
| 15 | 0.5 | 956 |
| 15 | 1.0 | 1,208 |
| 16 | 0.5 | 1,330 |

TABLE V-continued

| Compound | Amount | Embrittlement (Hours) |
|---|---|---|
| 16 | 1.0 | 1,393 |

EXAMPLE 8

The following diones were also evaluated

| Compound | Name | Structure |
|---|---|---|
| 17 | 1,10-Diphenyl-decane-1,3,8,10-tetrone | (structure shown) |
| 18 | 1,14-Diphenyl-tetradecane-1,3 12,14-tetrone | (structure shown) |

To a composition comprising
100 parts of high density polyethylene
0.5 parts of calcium stearate, and
100 parts of methylene chloride each of the above compounds was added at 2 amounts -- 0.1 parts and 0.5 parts. Sheets were prepared from each of the compositions and tested as described in Example 3. The results are given in the following table.

TABLE VI

| Compound | Amount | Embrittlement (Hours) |
|---|---|---|
| — | — | 1,476 |
| 17 | 0.1 | 718 |
| 17 | 0.5 | 810 |
| 18 | 0.1 | 678 |
| 18 | 0.5 | 618 |

A second composition was prepared comprising
100 parts of polypropylene,
0.5 parts of calcium stearate, and
100 parts of methylene chloride.
Each of the above compounds was also evaluated at two levels in this composition. These results are given in the following table.

TABLE VII

| Compound | Amount | Embrittlement (Hours) |
|---|---|---|
| — | — | 288 |
| 17 | 0.1 | 204 |
| 17 | 0.5 | 240 |
| 18 | 0.1 | 180 |
| 18 | 0.5 | 216 |

What is claimed is:
1. A photodegradable composition comprising:
a. a polyolefin, and
b. an aryl substituted 1,3-dione having the following formula:

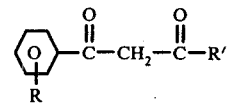

wherein R is selected from the group consisting of hydrogen, halogen, $C_1$ to $C_9$ alkyl, and $C_1$ to $C_9$ alkoxy, and R' is selected from the group consisting of $C_1$ to $C_{17}$ alkyl, cycloalkyl containing from 4 to 7 carbon atoms, and substituents represented by the following formula:

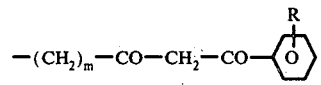

wherein m is an integer equal to from 1 to about 8 and R is as defined above
wherein the amount of dione is equal to from about .05 to 1.0% by weight based on the total weight of said composition.
2. A composition, as claimed in claim 1, wherein the polyolefin is polyethylene.
3. A composition, as claimed in claim 1, wherein the dione has the following formula:

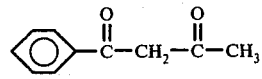

4. A film prepared from the composition of claim 1.